United States Patent [19]
Springer et al.

[11] Patent Number: 5,215,969
[45] Date of Patent: Jun. 1, 1993

[54] DOPAMINERGIC NEUROTROPHIC FACTOR FOR TREATMENT OF PARKINSON'S DISEASE

[75] Inventors: Joe E. Springer, Ambler, Pa.; Timothy J. Collier, Rochester, N.Y.

[73] Assignees: Hahnemann University, Philadelphia, Pa.; University of Rochester, Rochester, N.Y.

[21] Appl. No.: 804,340

[22] Filed: Dec. 9, 1991

Related U.S. Application Data

[63] Continuation-in-part of Ser. No. 392,733, Aug. 11, 1989, abandoned.

[51] Int. Cl.⁵ .............................................. A61K 37/02
[52] U.S. Cl. ........................................ 514/21; 514/2
[58] Field of Search .................................... 514/2, 21

[56] References Cited

U.S. PATENT DOCUMENTS 4,701,407 10/1987 Appel ...................................... 435/4

OTHER PUBLICATIONS

Collier et al. Experimental Neurology, vol. 114 pp. 343-350 (1991).
Theonen et al., Rev. Physiol. Biochem. Pharmacol., 109: 145-178 (1987).
Whittemore et al., Brain Research Review, 12: 439-464 (1987).
Tomozawa et al., Brain Research, 399: 111-124 (1986).
Windebank et al., Brain Research, 385: 197-200 (1986).
Dal Toso et al., J. Neuroscience: 8: 733-745 (1988).
Araujo et al., Brain Research, 484: 130-138 (1989).

*Primary Examiner*—Michael G. Wityshyn
*Assistant Examiner*—Choon Koh
*Attorney, Agent, or Firm*—Dann, Dorfman, Herrell and Skillman

[57] ABSTRACT

Dopaminergic Neurotrophic Factor (DNTF), derived from cells of the peripheral nervous system, is administered to patients suffering from Parkinson's Disease in an amount effective to facilitate survival of substantia nigra dopamine nerve cells.

12 Claims, No Drawings

DOPAMINERGIC NEUROTROPHIC FACTOR FOR TREATMENT OF PARKINSON'S DISEASE

BACKGROUND OF THE INVENTION

Pursuant to 35 U.S.C. §202(c), it is hereby acknowledged that the U.S. Government has certain rights in the invention described herein, which was made in part with funds from the National Institute of Health.

This application is a continuation-in-part of co-pending U.S. patent application Ser. No. 392,733, filed Aug. 11, 1989, now abandoned.

The present invention relates to a composition of matter, derived from cells of the peripheral nervous system, comprising dopaminergic neurotrophic factor, to a pharmaceutical preparation containing the dopaminergic neutrophic factor, and to its use in the treatment of Parkinson's disease.

Parkinson's disease is a neurodegenerative disorder of the basal ganglia affecting specific populations of neurons in the central nervous system. Symptoms of Parkinson's disease include tremor at rest, muscular rigidity, akinesia and bradykinesia.

The primary neuropathology associated with this disorder is the progressive and persistent loss of dopaminergic neurons originating in the substantia nigra and projecting into the striatum. This, in turn, leads to a substantial decrease in the enzymes responsible for the synthesis of the neurotransmitter, dopamine. The subsequent decrease in dopamine synthesis correlates with the onset and severity of the above-noted symptoms.

Evidence indicating that the loss of dopaminergic neurons is causally connected with the symptoms associated with Parkinson's disease was found in 1983. Specifically, certain drug abusers who injected a toxin, known as 1-methyl-4-phenyl-1,2,3,6-tetrahydropyridine (MPTP), as a heroin substitute developed signs of parkinsonism soon after injection. It was subsequently determined that MPTP is converted to a form (MPP+) that accumulates in substantia nigra dopamine neurons where it acts as a toxin destroying these neurons. The resultant loss of dopaminergic neurons was found to mimic the neuropathology observed in Parkinson's disease.

Studies have shown that Parkinson's disease, as well as other neurodegenerative disorders such as Alzheimer's disease and amyotrophic lateral sclerosis (ALS), may occur due to the loss or decreased availability of a neurotrophic substance specific for a particular population of neurons affected in each disorder. As used herein, "neurotrophic factor" refers to a substance or combination of substances whose primary function is to increase and/or maintain the survival of a neuronal population, but may also affect the outgrowth of neuron processes (neurite-promoting factors), and the metabolic activity of a neuron. The specific neurtrophic factor is synthesized, stored, and/or released from the target area of the degenerating neurons, bound and internalized by specific receptors, and transported in a retrograde fashion to the neuron body where it exerts its trophic effects well into adulthood. It may be the loss of such specific neurotrophic factors which is responsible for age-related declines in cell survival and/or function. While the cellular source remains unclear, there is evidence to suggest that neurons and glia are both capable of secreting neurotrophic factors.

Several putative neurotrophic factors effecting specific neuronal populations in the central nervous system have been reported. For example, it is postulated that Alzheimer's disease is the result of the loss or decreased availability of nerve growth factor (NGF), a polypeptide of approximately 13,000 dalton molecular weight in the monomer form. NGF is known to increase the survival, function and regeneration of cholinergic neurons in the basal forebrain. This population of cholinergic neurons has been shown to shrink and/or die in patients having Alzheimer's disease, and may be the primary neuronal defect responsible for the profound cognitive deficits associated with Alzheimer's disease. Recent studies have demonstrated that NGF is synthesized and released from the target areas of these cholinergic neurons, which are the hippocampal formation and the neocortex. Thoenen, H. et al., Rev. Physiol. Biochem. Pharmacol. 109:145–178 (1987); and Whittemore, S. R. et al., Brain Res. Rev. 12:439–464 (1987). Insofar as is known, there is no conclusive evidence that a loss of NGF production is the primary cause of degeneration of the basal forebrain cholinergic neurons. However, it has been proposed to treat Alzheimer patients by administering exogenous NGF, in order to increase the survival of degenerating neuronal populations.

At the present time, the therapy of choice for patients having Parkinson's disease is through stimulation of dopamine receptors in the striatum, which is the target area of substantia nigra neurons. This is achieved through "precursor drug therapy", involving the administration of $\beta$-(3,4-dihydroxy phenyl)-$\alpha$-alanine(L-DOPA/LEVODOPA), which passes the blood-brain barrier and is converted to dopamine. While this pharmacological approach is initially effective, L-DOPA treatment often becomes less effective over time and in many cases the patients' symptoms worsen.

Numerous neurotrophic factors, in addition to NGF, which produce biological effects in the central nervous system have been reported, and these will be more specifically discussed hereinbelow. Insofar as is known, however, there is no currently available method for rescuing degenerating dopaminergic neurons in the substantia nigra. In addition, the conditions responsible for the onset of the degeneration of these nerve cells have not been elucidated. Thus, there is currently no clearly effective cure for Parkinson's disease.

SUMMARY OF THE INVENTION

In accordance with one aspect of the present invention, there is provided a purified and concentrated form of dopaminergic neurotrophic factor (DNTF) derivable from cultured cells of the mammalian peripheral nervous system. DNTF comprises a polypeptide having molecular weight of between about 9,000 and 10,000 daltons and exhibits a neurotrophic effect on substantia nigra dopamine nerve cells. Among the notable properties of DNTF is its ability to increase the survival time of fetal non-mitotic dopamine nerve cells in culture and to increase in vivo expression of tyrosine hydrosylase in substantia nigra dopamine nerve cells exposed to said factor.

In accordance with another aspect of this invention, there is provided a pharmaceutical preparation for the treatment of Parkinson's disease which comprises, as the active agent, the aforesaid DNTF in an amount sufficient to increase the survival and function of dopamine nerve cells located in the substantia nigra and projecting to the striatum, and, possibly, to cause regeneration of these cells.

In accordance with a further aspect of the present invention, there is provided a method for treating patients having Parkinson's disease, which comprises administering to such patients the above-described DNTF.

The present invention represents a potentially important alternative to current therapy used for treatment of Parkinson's disease. The precursor drug therapy (L-DOPA) now in use does not provide a cure for Parkinson's disease, but rather is a method of treatment that may become ineffective and even detrimental with prolonged use. It is anticipated that treatment of Parkinson's patients with the dopamine neurotrophic factor of the invention will inhibit or halt the progress of the disease by reducing the degeneration and dysfunction of substantia nigra nerve cells. In addition, dopamine neurotrophic factor treatment may be useful in transplantation strategies where dopamine cells are transplanted as a means of replacing lost dopamine function. Specifically, dopaminergic neurotrophic factor may be administered in conjunction with central nervous system grafts of dopamine-synthesizing tissue in order to enhance the survival and function of the grafted tissue.

The dopaminergic neurotrophic factor of the invention that is responsible for the observed activity against Parkinson's disease appears to comprises a polypeptide of approximately 9,500 daltons in molecular weight. However, the possiblity that the factor may be glycosylated or associated with lipids has not been ruled out. Accordingly, the singular of the terms "agent", "component", "ingredient", or the like, as used herein in reference to the DNTF, also includes the plural.

Although numerous neurotrophic factors having biological effects in the central nervous system have previously been reported, including factors derived from cells of the peripheral nervous system, none of the factors obtained heretofore are believed to exhibit physical or biological properties identical to the dopaminergic neurotrophic factor of the invention, as will be shown hereinbelow. Moreover, attempts previously made to recover a DNTF from the striatum, prompted by evidence supporting its presence there, has not led to the successful isolation of such factor Tomozawa, Y. et al., *Brain Research,* 399:111-124 (1986).

DETAILED DESCRIPTION OF THE INVENTION

As noted above, the primary symptoms of Parkinson's disease are caused by a defect in a specific neurotransmitter system, the nigrostriatal dopamine system. Specifically, dopamine neurons in the substantia nigra degenerate, resulting in the loss of dopamine input to the striatum and the onset of characteristic movement abnormalities.

One possible explanation for the degeneration of the dopamine-containing nerve cells is that a specific dopamine neurotrophic factor becomes ineffective, unavailable or is no longer synthesized by the target regions in the striatum. In addition, most neurotrophic factors function through specific membrane-bound receptors located on presynaptic terminals. Alterations in the function of these receptors would tend to render the neurotrophic factor ineffective. In a normal, healthy individual, dopamine neurotrophic factor is released from the target region of these dopamine-containing substantia nigra nerve cells in the striatum. This factor is recognized and bound by specific receptors, then internalized as a complex and transported in a retrograde fashion to the cell body of the nerve cell where it functions to maintain dopamine neuron survival and normal homeostatic function. In the case of Parkinson's disease, by comparison, the striatum may no longer be providing an adequate supply of the dopaminergic neurotrophic factor, resulting in dopamine nerve cells that are no longer able to function adequately and may eventually die due to the loss of the dopaminergic neurotrophic factor.

The DNTF used in the practice of this invention comprises a soluble polypeptide of molecular weight approximately 9,500 daltons which is extractable from cells of the peripheral nervous system. While the peripheral nerve is not a target of the central nervous system dopamine nerve cells, the cells associated with the peripheral nerve are known to synthesize and secrete a number of different trophic factors, e.g. NGF, especially following denervation.

The extraction of DNTF is performed on peripheral nerve preparations that have been incubated in low-serum or serum-free culture medium. In a preferred embodiment, Schwann cells (which are derived from the sciatic nerve) are utilized. Protease inhibitors, such as leupeptin, may be included in the culture medium in order to minimize the degradation of proteins secreted by the peripheral nerve cells.

A crude preparation of DNTF is recoverable from the culture medium using conventional molecular weight exclusion techniques. Extraction has been satisfactorily performed using centrifugation filters with molecular weight exclusion capabilities. For example, Centricon ®-10 and −30 (Amicon) centrifuge filtration tubes may be used to obtain fractions from the peripheral nerve preparation. This procedure allows for the isolation of a first fraction comprising molecules of molecular weight less than 10 kilodaltons (Centricon-10) and a second fraction comprising molecules of molecular weight less than 30 kilodaltons (Centricon-30). The greatest amount of dopamine neurotrophic activity is exhibited by the filtrate obtained from the Centricon-10 tubes. The second fraction (molecular weight range between 10,000–30,000 daltons) includes a molecule or molecules that cause(s) dramatic increases in the outgrowth of neuron processes in dopamine-containing nerve cells in culture.

Additional conventional processing steps may be implemented to further isolate and purify the desired product. A preferred purification scheme is described in detail in Example 1(b) below. Because the DNTF polypeptide is a relatively small protein, it may be isolated using reverse phase, high-performance liquid chromatography (RPHPLC). Alternatively, the polypeptide may be isolated using a variety of other techniques including ion exchange chromatography or absorption chromatography. Large scale isolation may be performed using affinity chromatography, preferably with an appropriate monoclonal antibody having binding affinity for the DNTF polypeptide. The desired product is then sterilized, lyophilized and its neurothropic activity determined using the culture bioassay described below (see Example 2).

The molecular weight of purified DNTF polypeptide is approximately 9,500 daltons. The purified polypeptide has been found to have the following additional characteristics: (1) it is a basic substance, as it does not bind to anion exchange resins such as DEAE cellulose, but can be eluted from carboxymethyl cellulose using 0.5 M NaCl; and (2) the 9,500 dalton polypeptide-containing band can be excised from an SDS gel (0.1% SDS), and the polypeptide eluted into culture media for treatment of dopaminergic neurons, and the polypeptide present in the 9,500 dalton band exhibits the biological activity of DNTF.

A partial amino acid N-terminal sequence of the DNTF polypeptide was performed using the Edman degradation procedure. The 15 amino acid sequence consisted of Sequence ID No. 1 below: Xaa-Glu-Asp-Thr-Ser-Asn-Ile-Ala-Val-Ala-Ser-Gly-Xaa-Xaa-Pro, wherein Xaa represents an amino acid of mammalian proteins, the identity of which was not determined in the sequencing procedure.

The partial sequence was searched against the GEN-BANK and EMBL protein databases, and was found to be unique.

The dopamine neurotrophic activity of the recovered material is readily determined via bioassay. One method of assaying for neurotrophic activity is to determine biological activity in cultures of dopaminergic nerve cells. The DNTF polypeptide of the invention has been found to exhibit selective survival and survival-related effects, i.e. production of dopamine-synthesizing enzymes, on dopamine nerve cells using the culture bioassay. Other measures of dopaminergic neurotrophic activity, besides survival, include cell growth and metabolic functions associated with normal homeostatic function, such as high affinity dopamine uptake. Following incubation with fractions exhibiting dopaminergic neurotrophic activity, dissociated cell cultures are stained using tyrosine hydroxylase immunocytochemistry. Tyrosine hydroxylase is an enzyme necessary for the production of dopamine. Thus, by using antibodies to tyrosine hydroxylase, dopamine-containing nerve cells may be identified. Once the dopamine-containing nerve cells are identified, measures of cell size can be performed on culture treated with DNTF, as opposed to control treated cultures.

Changes in the levels of tyrosine hydroxylase messenger RNA can also provide a measure of dopamine neuronal function. Recent advances in molecular biology, such as in situ hybridization, permit quantitative analysis of single genes in single neurons. Such techniques make it possible to study the effects of dopaminergic neurotrophic factor on tyrosine hydroxylase gene expression In vitro and in vivo and are currently being implemented toward that end.

Once dopamine is released from the presynaptic terminal, it is degraded by monoamine oxidase or taken up again into the presynaptic terminal by a high affinity uptake mechanism. Using radioactive ($^3$H) dopamine, the high-affinity uptake of dopamine can be determined in cultures treated with dopaminergic neurotrophic factor or control solutions. Increases in dopamine uptake can indicate increased dopamine synthesis and release, a measure of metabolic function in such nerve cells.

Experiments have been performed, both in vitro and in vivo which demonstrate the neurotrophic effect of DNTF on substantia nigra dopamine nerve cells and its potential for effectively treating Parkinson's Disease. The nature of these experiments and their results are described hereinbelow.

Several experiments have been performed in vivo using rats that have sustained unilateral damage to the nigro-striatal pathway. This damage results in a massive loss of dopamine input to the striatum, and a behavorial syndrome consisting of amphetamine-induced rotation towards the side of damage. This rotation effect has become a classic model for screening dopamine-related compounds. Indeed, it has been shown in numerous laboratories that transplantation of fetal dopamine neurons can cause reversal of this behavorial deficit. Facilitation of this behavorial recovery over time can be accomplished using co-grafts of peripheral nerve capable of secreting DNTF and mesencephalic dopamine synthesizing cells. It appears that the peripheral nerve secretions (including DNTF) continue to affect the dopamine cells in the host following transplantation.

Other experiments conducted to date include the transplantation of peripheral nerve segments into aging test animals with the compromised dopamine system, i.e. decreased number of dopamine-containing neurons and decreased dopamine synthesis and content. The peripheral nerve graft greatly increases tyrosine hydroxylase staining in remaining substantia nigra neurons, as well as the number of tyrosine hydroxylase-containing nerve fibers.

These experimental results indicate that DNTF is most likely a soluble factor released in vitro and in vivo by peripheral nerves, which may be transported in a retrograde fashion to the cell bodies of substantia nigra neurons, so as to enhance their survival and function.

As noted above, numerous neurotrophic factors exhibit biological effects in the central nervous system, including factors derived from the peripheral nervous system. Some of the well-characterized factors are listed below in Table 1. DNTF is distinctly different from all of the neurotrophic factors listed in Table 1, notwithstanding that it shares certain characteristics with some of them.

TABLE 1

Purified and partially-purified neurotrophic factors, their effects in the central nervous system, and selected physical properties

| FACTOR | EFFECTS | PROPERTIES |
| --- | --- | --- |
| Nerve growth factor (NGF)* | survival of cholinergic neurons, neurite induction | MW 13,000 pI 10.0 |
| Ciliary neurotrophic factor (CNTF)* | survival, neurite outgrowth | MW 20,400 pI 5.0 |
| Brain-derived neurotrophic factor (BDNF)* | survival, (additive with NGF) | MW 12,300 pI 10.1 |
| Insulin-like growth factor-II (IGF-II) | survival, neurite outgrowth | MW 7,100 |
| Basic fibroblast growth factor (bFGF)* | survival, neurite outgrowth | MW 16,400 pI 9.6 |
| Acidic fibroblast growth factor (aFGF) | neurite outgrowth | MW 15,800 pI 5.0 |
| Striatal-derived neuronotrophic factor | survival of dopamine cells, neurite outgrowth | MW 14,000 |
| Striatal extract factors | survival of dopamine cells, neurite outgrowth, dopamine uptake | MW 1500-2200 |

The asterisk indicates a factor derived from cells of the peripheral nervous system.

One of the characteristics of a true neutrophic factor is the ability to increase the survival of central nervous system (CNS) neurons. Based on this criterion, aFGF, listed in Table 1, is not a true neutrophic factor, but rather may be regarded as a "neurite-promoting" factor. Similarly, numerous other factors, including, for example, fibronectin, collagen and laminin, are able to promote neurite outgrowth, without appreciably influencing the survival of the neuronal population.

Among the neurotrophic factors, listed in Table 1, CNTF is synthesized by denervated peripheral nerves and influences the survival and outgrowth of numerous neuronal populations including cilary neurons, sympathetic neurons, dorsal root ganglia and some centrally-derived neurons. However, the DNTF of the present invention is lower in molecular weight than CNTF (approximately 9,500 for the DNTF polypeptide as compared to 20,400 for CNTF).

Another factor that may be secreted by peripheral nerves is bFGF. Although bFGF may be considered a true neurotrophic factor, at least two characteristics serve to distinguish bFGF from DNTF. First, the molecular weight of bFGF is greater than 10,000 daltons, while the molecular weight of the DNTF polypeptide is about 9,500 daltons. Second, bFGF contains a heparin sulfate binding domain. Fractions of peripheral nerve conditioned medium that have been passed over a heparin sulfate column (removing bFGF from the fraction) continued to enhance neuron survival and neurite outgrowth in cultured dopamine neurons. These data indicate that DNTF is not related to bFGF, since it appears to contain no heparin binding site and presumably exhibits its activity after bFGF has been removed from peripheral nerve cell culture fluids.

Gangliosides, a family of glycosphingolipids present in nerve tissues, may also be secreted by peripheral nerves. While there is no evidence to indicate that gangliosides function as a survival or neurotrophic factor, it appears that the presence of gangliosides may potentiate neurotrophic activity. For example, gangliosides have been shown to potentiate the effects of NGF on cultured basal forebrain cholinergic neurons. In addition, ganglioside treatment has been shown to enhance the regeneration (but not survival) of substantia nigra dopamine neurons following damage. Thus, the effects of gangliosides are not as specific as DNTF, and require the presence of other appropriate trophic influences to be effective.

A recent report describes a peripheral nerve-derived soluble factor(s) that increases the survival and neurite outgrowth of sensory neurons in culture. Windebank, A. J. et al., *Brain Research*, 385:197-200 (1986). While this report intimitates that the factor described therein is novel, the molecular weight and biological properties given are similar to CNTF, listed in Table 1 above.

Considering the striatum-recovered factors listed in Table 1, DNTF differs from striatal-derived neurotrophic factor in that its molecular weight is less than 14,000. Moreover, it has been suggested that striatal-derived neurotrophic factor may not be unique, but in fact exhibits properties not unlike those of BDNF and bFGF. Dal Toso, R. et al., *J. Neurosci.*, 8:733-745 (1988). Other factors are found in the striatum that fall within the molecular weight range of 1,500-2,200 daltons. These factors, however, are also found in high concentrations in non-dopaminergic brain regions, such as the hippocampus, amygdala and cerebral cortex, and also influence the high affinity uptake of gamma-amino-n-butyric acid (GABA). These data indicate that striatal extract factors may not necessarily be specific to dopamine neurons. The use of striatal factors as a diagnostic and therapeutic tool in the treatment of Parkinson's Disease is the subject of a separate patent application. See U.S. patent application Ser. No. 444,293, filed Nov. 24, 1982, and related applications.

Unlike DNTF, NGF does not exhibit a neurotrophic effect on substantia nigra dopamine nerve cells. The molecular weight of NGF is also higher than that of DNTF. DNTF is similarly distinguishable from BDNF on the basis of their relative molecular weights. IGF-II is produced in the central nervous system almost exclusively in the astroglia. The role of IGF-II in the peripheral nervous system appears to be related to synapse formation and denervated-induced fiber growth during development and regeneration. Specifically, IGF-II levels are highest in the target region (muscle fiber) during pre-and early post natal development. Transection of the sciatic nerve also results in increased IGF-II levels in mature denervated muscle fibers. IGF-II has been shown to increase the survival of NGF-sensory and sympathetic neurons in culture. However, direct evidence for IGF-II as a survival factor in the central nervous system is lacking.

Another insulin-related growth factor, IGF-I also is present in the central nervous system and is synthesized in neuronal and non-neuronal cells. IGF-I, which has a molecular weight of about 7,600 daltons, has been shown to undergo retrograde transport in the rat sciatic nerve and may play a role in peripheral nerve regeneration. In addition, IGF-I can act as a survival factor for cortical neurons in transferrin-supplemented medium. At the present time, no effects of IGF-I on survival or neurite outgrowth Of cultured dopamine neurons has been reported. Moreover, a recent study has shown that binding sites for IGF-I in the central nervous system are associated with cholinergic, and not dopaminergic brain regions. Araujo, D. M. et al., *Brain Res.*, 484:130-138 (1989). Therefore, given the published results of this study and our own test results, it appears that DNTF is not related to the insulin family of growth factors.

In sum, while there are numerous neutrophic factors that have biological activities in the central nervous system, as set forth in Table 1 above, the apparent differences in properties between such factors and DNTF provides compelling evidence of the uniqueness of DNTF. Morever, the uniqueness of the partial amino acid sequence of DNTF is compelling evidence that DNTF is indeed a novel molecule.

DNTF may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined emperically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the active ingredient of DNTF, its use in the pharamceutical preparation of the invention is contemplated.

It is especially advantageous to formulate the pharmaceutical preparation in dosage unit form for ease of administration and uniformity of dosage. "Dosage unit form" as used herein, refers to a physically discrete unit of the pharmaceutical preparation appropriate for the patient undergoing treatment. Each dosage should contain the quantity of active ingredient calculated to produce the desired therapeutic effect in association with the selected pharmaceutical carrier. The appropriate dosage unit to be administered for facilitating survival of substantia nigra dopamine nerve cells may be routinely determined by those skilled in the art. It is expected that the standard dosage unit will contain less than a milligram of the active ingredient.

The pharmaceutical preparation is preferably administered parenterally, e.g. by introduction into the central nervous system of the patient. Such administration may be accomplished by intracerebroventricular infusion. Patients may also be treated with DNTF by transplanting into the striatum cells of the peripheral nervous system capable of releasing DNTF. Such cells may be cotransplanted with dopamine-synthesizing cells of the central nervous system, such as mesencephalic dopamine synthesizing cells. The treatments just described may also be administered in conjunction with one another. For example, dopamine synthesizing cells of the central nervous system may be transplanted into the striatum of a patient who is simultaneously being administered the pharmaceutical preparation of the invention. Non-parenteral routes may also be useful in administering DNTF, including oral, intranasal, rectal as well as opthalmic administration. The pharmaceutical preparation of the invention may be administered at appropriate intervals, until the symptoms of the disease are no longer evident, after which the dosage may be reduced to a maintenance level. The appropriate interval of administration in a particular case would normally depend on the condition of the patient. As used herein, the term "patient" includes both humans and animals.

The following examples are provided to describe the invention in further detail. These examples are intended to illustrate and not to limit the invention.

EXAMPLE 1

Methods for Isolation and Purification of DNTF a. Crude Preparations

Rat sciatic nerves (approximately 2.5-3.0 cm in length) are placed in 1.0 ml. of sterile, serum-free culture medium containing protease inhibitors and incubated at 37° C. in a humid environment containing 95% air and 5% $CO_2$. After three days of incubation, the conditioned medium was removed, frozen at $-20°$ C. and the culture medium was replaced with new medium. The removal and replacement process was repeated for two more cycles, so that 3.0 ml of conditioned medium was obtained. The conditioned medium was then placed into Centricon ®-10 and $-30$ centrifuge tubes and centrifuged for 1½ hours at 4° C. A total of 3 fractions were isolated using this technique. A first fraction contained compounds of molecular weight of 10,000 daltons or less and included the DNTF. A second fraction contained compounds of molecular weight of 30,000 daltons or less, which included substances that dramatically increased the outgrowth of neurite processes, i.e. neurite number, length and branching, in dopamine-containing neurons and culture. A third fraction comprised compounds of molecular weight in excess of 30,000 daltons which included substances which exhibited a neurotoxin-like effect on dopamine-containing neurons. Because DNTF is found in the fraction recovered in the Centricon-10 centrifuge tube, isolation of DNTF can be initiated using this procedure. The DNTF-containing fraction was sterilized by passage through a 0.2 um filter, lyophilized and subjected to neurotrophic activity determination by culture bioassay.

b. Purified DNTF

The dopaminergic neurotropic factor of the present invention was purified from Schwann cells (which are derived from the sciatic nerve of the mammalian peripheral nervous system), according to the following procedure. Schwann cells were plated at an initial plating density of 200,000 cells/cc in low serum culture medium and grown to confluence (1 week). The culture medium was collected and proteins precipitated with 70% ammonium sulfate, then centrifuged and the pellet resuspended in 0.15 M phosphate buffered saline (PBS, pH 7.4). The resuspended protein solution was dialyzed against 0.15 M PBS overnight at 4° C., using dialysis tubing with a molecular weight cut-off of 3,500 daltons. The dialyzate was then subjected to molecular weight separation by gel filtration on Sephadex G-50. Protein peaks were collected, reprecipitated in 70% ammonium sulfate, resuspended and dialyzed against PBS as described above. The dialyzate was adsorbed on a carboxymethyl cellulose ion exchange matrix, and eluted with 0.5 M NaCl. The ion exchange eluant was subjected to electrophoresis on a 15% SDS polyacrylamide gel, and stained using standard silver staining procedures.

The molecular weight of purified DNTF polypeptide has been determined to be approximately 9,500 daltons, using SDS polyacrylamide gel electrophoresis. The purified dopaminergic neurotrophic factor has also been found to have the following characteristics: (1) it is a basic protein, as it does not bind to anion exchange resins such as DEAE cellulose, but can be eluted from carboxymethyl cellulose using 0.5 M NaCl; and (2) the 9,500 dalton protein band can be excised from an SDS gel (0.1% SDS), and the protein eluted into culture media for treatment of dopaminergic neurons, and the protein present in the 9,500 dalton band exhibits the biological activity of DNTF.

The partial amino acid N-terminal sequence of the 9,500 dalton DNTF protein was performed using the Edman degradation procedure. The 15 amino acid sequence consisted of Sequence ID No. 1 below: Xaa-Glu-Asp-Thr-Ser-Asn-Ile-Ala-Val-Ala-Ser-Gly-Xaa-Xaa-Pro, wherein Xaa represents an amino acid of mammalian proteins, the identity of which was not determined in the sequencing procedure.

The partial sequence was searched against the GEN-BANK and EMBL protein databases, and was found to be unique. Thus, DNTF is indeed a novel molecule derivable from peripheral nervous system cells and having specific neurotrophic properties on ventral mesencephalon neurons.

EXAMPLE 2

Tissue Cultures

Dissociation cultures of dopamine nerve cells were obtained using standard protocols. Specifically, 25 0.2-0.4 mm pieces of rat ventral mesencephalon (which included A8-A10 dopamine nerve cells) were disected from embryonic day 13-16 rats. At this stage of development, the dopamine nerve cells were post mitotic, but did not yet innervate the striatum. Dissociated cell cultures were prepared by triturating the tissue in the presence of DNase (1 mg/ml) and trypsin (0.25 mg/ml). Cells were washed in Opti-MEM medium (Gibco) supplemented with 10% fetal bovine serum (FBS) and then plated in 16 mm diameter plastic wells at a density of 500,000 cells per well containing 1.0 ml Opti-MEM and 10% FBS. Cells were allowed to equilibrate in this solution for 72 hours, at which time the cells were switched to 1.0 ml serum-free Opti-MEM containing a 100 ul solution of DNTF solution. These cells were maintained at 37° C in 95% air-5% CO2 for a period of 7 days, with the DNTF-containing culture medium being replaced every other day. Thus, the cells received three treatments of DNTF-containing culture medium.

EXAMPLE 3

DNTF Activity In Vitro

Cultures of mesencephalic nerve cells were stained for tyrosine hydroxylase (TH) to identify dopaminergic nerve cells. Cultures were fixed with 5% acrolein, and prepared for immunocytochemistry utilizing the Vectastain ABC technique (Vector Laboratories, Inc., Burlingame, Calif.). In this study, TH was utilized as a marker for developing midbrain DA neurons. TH antibody was obtained from Eugene Tech (Allendale, N.J.), and used in a dilution of 1:2,500.

Cultures treated for 10-14 days with the <10,000 molecular weight fraction obtained in Example 1(a) exhibited a 1.8-8.0 fold increase in dopamine cell number compared to control treated cultures. Cultures treated with the 10,000-20,000 molecular weight fraction obtained in Example 1(a) also exhibited an increase in dopamine cell survival, but not to the same extent as that observed for the first fraction (1.5 for the second fraction, as compared with 1.8-8.0 for the first fraction). This is probably due to the dilution of the DNTF in the higher molecular weight fraction. However, extensive neurite outgrowth was observed in cultures that were treated with the 10,000-20,000 m.w. from Example 1(a), as compared with all other treatments. While this neurite-promoting factor has not been conclusively identified, it exhibits properties similar to CNTF (see Table 1 above), which is found in relatively high concentrations in peripheral nerve extracts.

The effect of DNTF could not be blocked with antiserum to NGF or laminin and was partially induced by exposing the cultured dopamine nerve cells to the 10,000-20,000 molecular weight fraction from Example 1(a) for only 2 days, followed by 5 additional days in serum-free medium only. Thus, constant presence of DNTF may not be necessary to provide an effective level of neuron survival and function.

DNTF polypeptide purified by the method described in Example 1(b) exerted a similar effect on mesencephalic nerve cell number and survival.

EXAMPLE 4

DNTF Activity In Vivo a. Crude Preparation

The low molecular weight fraction from Example 1(a) has been tested using three different conditions to determine its effects in vivo. Rat sciatic nerve, including the tibial and peroneal branches were stripped of the surrounding epineurium, cut into 5.0 mm segments, and washed repeatedly in sterile calcium-magnesium free medium containing 0.1% glucose, 100 ug/ml streptomycin and 2.5 ug/ml fungizone. These nerve segments were then loaded into the lumen of sterilized Amicon XM-50 fibers (1.1 mm ID; cut into 4.5 mm lengths), using polyethylene (PE 60) tubing attached to a 25 gauge needle and a 1.0 cc syringe. The ends of the Amicon fibers were sealed by pinching with heated forceps, and then placed in RPMI 1,640 medium supplemented with 10% fetal calf serum, 5% normal horse serum, 2 mM L-glutamine, 0.45% glucose, 1 mM sodium pyruvate, 50 units per ml penicillin, and 50 ug/ml streptomycin. The nerve-containing tubes were incubated in this solution for 1-2 days in a humid chamber of 95% air, 5% C.°2 at 37° C.

The hollow polymer fibers serve as carriers for subsequent transplantation of the nerve segments into the central nervous system. The polymer fibers comprise a semiporous membrane that allows for the exclusion of molecules of specified molecular weights. The membrane of the polymer fibers used in this experiment allowed the passage of molecules up to 50,000 daltons. The nature of the polymer is such as to inhibit rejection of the transplant by the immune system.

The nerve tube implants thus prepared were transplanted into the lateral cerebral ventrical of young and aging normal rats for 2, 4, 8 or 10 weeks. In addition, the nerve tube implants were transplanted into young adult rats with unilateral lesions of the nigro-striatal dopamine system and co-grafts of fetal dopamine nerve cells (embryonic day 14). Lesions of the nigro-striatal dopamine system result in a well characterized unilateral rotation when the animals are challenged with dopamine agonists such as amphetamine. Transplants of fetal dopamine neurons have been found to reinnervate target areas denervated by the lesions, and to reverse the behavorial rotation.

In brain sections of animals that received only the nerve tube transplants, tyrosine hydroxylase staining was enhanced in the dopamine-containing neurons in the substantia nigra, as well as in nerve fibers located in the target region of these neurons. This effect was observed at 4, 8, and 10 weeks, but not at 2 weeks following transplantation. The presence of enhanced tyrosine hydroxylase staining in neurons distant to the nerve tube implant indicate that DNTF is a soluble factor that is transported specifically in dopamine-containing nerve cells.

Co-grafts of nerve tubes with fetal dopaminergic neurons into animals with unilateral lesions of the nigro-striatal dopamine system resulted in enhanced behavorial recovery as determined using the amphetamine-induced rotation. Immunohistochemical evaluation of the brain revealed enhanced tyrosine hydroxylase staining of grafted neuron cell bodies and axons. Invariably, fibers from the grafted neurons grew in the direction of the nerve tube implant, suggesting some "chemotactic" property. This phenomenon is not unexpected, for when a soluble source of a trophic factor is released from the nerve tube, the concentration of the trophic factor will be highest in proximity to the nerve tube, with concentration decreasing as the distahce from the nerve tube increases. In this case, the axons of the grafted nerve cells were attracted toward the gradient containing the highest concentration of trophic support.

b. Purified DNTF

The purified DNTF polypeptide from Example 1(b) has been tested to determine its effect in vivo. The 0.5 molar NaC eluent from Example 1(b) was prepared for in vivo testing by further dialysis against PBS. The dialyzed DNTF polypeptide was infused into the lateral cerebral ventrical of normal rats continuously over a 2-week period. Continuous infusion was accomplished by the use of a miniosmotic pump containing the purified DNTF.

Three (3) weeks following termination of the infusion period, the animals were sacrificed and brain sections were subjected to TH staining, as described in Example 3. Brain sections which had been subjected to DNTF infusion were compared with corresponding non-infused sections from the other side of the brain. An increase in TH staining intensity, as well as an increase in the number of fibers, was observed in the DNTF-infused brain sections, but not in the sections not subjected to DNTF infusion.

The in vivo test data indicate that DNTF treatment in patients having Parksinson's Disease would provide a valuable alternative to present therapy by facilitating dopamine neuron survival in the substantia nigra, which present therapy is unable to achieve.

While the various aspects of the present invention have been described and exemplified above in terms of certain preferred embodiments, various other embodiments may be apparent to those skilled in the art. For example, while the DNTF of the invention is derivable from cells of the peripheral nervous system according to the isolation and purification procedures described above, it may also be derivable from such cells using recombinant DNA techniques. Thus, it is quite possible that the gene responsible for DNTF expression could be isolated, cloned, and expressed in a suitable host cell to enable large scale production of biologically active DNTF. Since the same gene would be responsible for production of both the "natural" and "recombinant" proteins, their pharmacological effect would be expected to be substantially equivalent. This invention is, therefore, not limited to the embodiments specifically described and exemplified, but is capable of variation and modification, without departing from the scope and spirit of the present invention, as set forth in the following claims.

What is claimed is:

1. A purified form of soluble dopaminergic neurotrophic factor derived from cultured cells of the mammalian peripheral nervous system, said factor comprising a polypeptide of molecular weight between about 9,000 and about 10,000 daltons, said factor being capable of increasing the survival time of fetal, non-mitotic dopamine nerve cells in culture, and of increasing in vivo expression of tyrosine hydroxylase in substantia nigra dopamine nerve cells exposed to said factor, said factor having a neurotrophic effect on substantia nigra dopamine nerve cells.

2. A factor as claimed in claim 1, having a molecular weight of about 9,500 daltons.

3. A factor as claimed in claim 2, wherein the N-terminal portion of said polypeptide comprises the amino acid sequence ID No. 1: Xaa-Glu-Asp-Thr-Ser-Asn-Ile-Ala-Val-Ala-Ser-Gly-Xaa-Xaa-Pro, wherein Xaa represents an amino acid of mammalian proteins.

4. A factor as claimed in claim 1, derived from Schwann cells.

5. A factor as claimed in claim 1, which is derived via recombinant DNA techniques.

6. A pharmaceutical preparation for the treatment of Parkinson's Disease which comprises, as an active ingredient, a purified form of soluble dopaminergic neurotrophic factor derived from cultured cells of the mammalian peripheral nervous system, said factor comrpising a polypeptide of molecular weight between about 9,000 and about 10,000 daltons, said factor being capable of increasing the survival time of fetal, non-mitotic dopamine nerve cells in culture, and of increasing in vivo expression of tyrosine hydroxylase in substantia nigra dopamine nerve cells exposed to said factor, said factor having a neurotrophic effect on substantia nigra dopamine nerve cells, and a biologically acceptable medium.

7. A pharmaceutical preparation as claimed in claim 6 wherein said biologically acceptable medium is a liquid in which said active ingredient is soluble.

8. A method for treating patients having Parkinson's Disease, which comprises administering to said patients the pharmaceutical preparation of claim 6.

9. A method as claimed in claim 8, wherein said pharmaceutical preparation is administered by introduction into the central nervous system of said patients.

10. A method as claimed in claim 9 wherein said pharmaceutical preparation is administered by intracerebroventricular infusion.

11. A purified form of soluble dopaminergic neurotrophic factor derived from cultured cells of the mammalian peripheral nervous system, said factor comprising a polypeptide, the N-terminal portion of said polypeptide having the amino acid sequence ID No. 1: Xaa-Glu-Asp-Thr-Ser-Asn-Ile-Ala-Val-Ala-Ser-Gly-Xaa-Xaa-Pro, wherein Xaa represents an amino acid of mammalian proteins, said factor being capable of increasing the survival time of fetal, non-mitotic dopamine nerve cells in culture, and of increasing in vivo expression of tyrosine hydroxylase in substantia nigra dopamine nerve cells exposed to said factor, said factor having a neurotrophic effect on substantia nigra dopamine nerve cells.

12. A factor as claimed in claim 11, having a molecular weight between about 9,000 and about 10,000 daltons.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 15 amino acids
      (B) TYPE: amino acid
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
      (A) ORGANISM: Rat
      (F) TISSUE TYPE: Sciatic nerve
        (G) CELL TYPE: Schwann cells (xi) SEQUENCE DESCRIPTION: SEQ ID NO:1:

Xaa Glu Asp Thr Ser Asn Ile Ala Val Ala Ser Gly Xaa Xaa Pro
1               5                   10                  15